United States Patent
Furst

(10) Patent No.: US 8,769,794 B2
(45) Date of Patent: Jul. 8, 2014

(54) SPECIALLY CONFIGURED AND SURFACE MODIFIED MEDICAL DEVICE WITH CERTAIN DESIGN FEATURES THAT UTILIZE THE INTRINSIC PROPERTIES OF TUNGSTEN, ZIRCONIUM, TANTALUM AND/OR NIOBIUM

(75) Inventor: Joseph G. Furst, Lyndhurst, OH (US)

(73) Assignee: MICO Innovations, LLC, Rockville Centre, NY (US)

(*) Notice: Subject to any disclaimer, the term of this patent is extended or adjusted under 35 U.S.C. 154(b) by 980 days.

(21) Appl. No.: 12/441,213

(22) PCT Filed: Sep. 21, 2007

(86) PCT No.: PCT/US2007/079119
§ 371 (c)(1),
(2), (4) Date: Sep. 17, 2009

(87) PCT Pub. No.: WO2008/036870
PCT Pub. Date: Mar. 27, 2008

(65) Prior Publication Data
US 2010/0305682 A1 Dec. 2, 2010

Related U.S. Application Data

(60) Provisional application No. 60/846,154, filed on Sep. 21, 2006.

(51) Int. Cl.
*B23P 25/00* (2006.01)
(52) U.S. Cl.
USPC ............................................. 29/458; 623/1.13

(58) Field of Classification Search
USPC ..................... 29/458; 623/1.15, 1.2, 1.3, 1.31
See application file for complete search history.

(56) References Cited

U.S. PATENT DOCUMENTS

| | | | | |
|---|---|---|---|---|
| 5,366,504 A | * | 11/1994 | Andersen et al. | 623/1.5 |
| 5,609,629 A | * | 3/1997 | Fearnot et al. | 623/1.42 |
| 5,630,840 A | * | 5/1997 | Mayer | 623/66.1 |
| 5,674,242 A | * | 10/1997 | Phan et al. | 606/198 |
| 5,972,027 A | * | 10/1999 | Johnson | 623/1.42 |
| 6,017,362 A | * | 1/2000 | Lau | 623/1.2 |
| 6,206,916 B1 | * | 3/2001 | Furst | 623/1.46 |
| 6,238,491 B1 | * | 5/2001 | Davidson et al. | 148/237 |
| 6,327,772 B1 | * | 12/2001 | Zadno-Azizi et al. | 29/557 |
| 6,436,133 B1 | | 8/2002 | Furst et al. | |
| 6,442,822 B1 | * | 9/2002 | Liprie | 29/460 |

(Continued)

FOREIGN PATENT DOCUMENTS

| | | |
|---|---|---|
| JP | 2003-88590 | 3/2003 |
| WO | WO 02/05863 A1 | 1/2002 |

(Continued)

OTHER PUBLICATIONS http://www.thefreedictionary.com/passivation; p. 1, Passivation definition.*

(Continued)

*Primary Examiner* — Jermie Cozart
*Assistant Examiner* — Bayan Salone
(74) *Attorney, Agent, or Firm* — Fay Sharpe LLP

(57) ABSTRACT

Medical devices having special geometrical design features and possible surface modifications and can be comprised of niobium, tantalum, zirconium and/or tungsten alloy which is useful in treating a body passageway.

10 Claims, 11 Drawing Sheets

(56) References Cited

U.S. PATENT DOCUMENTS

| | | | |
|---|---|---|---|
| 6,451,052 B1* | 9/2002 | Burmeister et al. | 623/1.16 |
| 6,478,815 B1* | 11/2002 | Alt | 623/1.15 |
| 6,514,284 B1* | 2/2003 | Cheng | 623/1.15 |
| 6,527,802 B1* | 3/2003 | Mayer | 623/1.49 |
| 6,562,065 B1* | 5/2003 | Shanley | 623/1.15 |
| 6,565,599 B1* | 5/2003 | Hong et al. | 623/1.15 |
| 6,629,994 B2* | 10/2003 | Gomez et al. | 623/1.15 |
| 6,638,301 B1* | 10/2003 | Chandrasekaran et al. | 623/1.34 |
| 6,656,220 B1* | 12/2003 | Gomez et al. | 623/1.15 |
| 6,726,712 B1* | 4/2004 | Raeder-Devens et al. | 623/1.11 |
| 6,749,628 B1* | 6/2004 | Callol et al. | 623/1.15 |
| 6,876,712 B1* | 4/2005 | Liprie | 376/158 |
| 6,929,657 B2* | 8/2005 | Gomez et al. | 623/1.11 |
| 6,935,404 B2* | 8/2005 | Duerig et al. | 164/95 |
| 7,090,694 B1* | 8/2006 | Morris et al. | 623/1.15 |
| 7,135,039 B2* | 11/2006 | De Scheerder et al. | 623/1.42 |
| 7,217,286 B2* | 5/2007 | Falotico et al. | 623/1.42 |
| 7,223,286 B2* | 5/2007 | Wright et al. | 623/1.42 |
| 7,229,473 B2* | 6/2007 | Falotico et al. | 623/1.42 |
| 7,278,195 B2* | 10/2007 | Baum et al. | 29/419.2 |
| 7,335,229 B2* | 2/2008 | Alt et al. | 623/1.15 |
| 7,452,501 B2* | 11/2008 | Furst et al. | 420/429 |
| 7,452,502 B2* | 11/2008 | Furst et al. | 420/429 |
| 7,465,315 B2* | 12/2008 | Morris et al. | 623/1.15 |
| 7,488,444 B2* | 2/2009 | Furst et al. | 420/429 |
| 7,607,208 B2* | 10/2009 | Curcio et al. | 29/458 |
| 7,648,590 B2* | 1/2010 | Furst et al. | 148/423 |
| 7,648,592 B2* | 1/2010 | Furst et al. | 148/423 |
| 8,043,361 B2* | 10/2011 | Dicarlo et al. | 623/1.18 |
| 8,070,796 B2* | 12/2011 | Furst et al. | 623/1.42 |
| 8,114,151 B2* | 2/2012 | Kocur et al. | 623/1.42 |
| 2002/0007209 A1* | 1/2002 | Scheerder et al. | 623/1.15 |
| 2002/0144757 A1* | 10/2002 | Craig et al. | 148/327 |
| 2003/0018380 A1* | 1/2003 | Craig et al. | 623/1.15 |
| 2003/0088308 A1* | 5/2003 | Scheuermann et al. | 623/1.15 |
| 2003/0125802 A1* | 7/2003 | Callol et al. | 623/1.35 |
| 2004/0000046 A1* | 1/2004 | Stinson | 29/426.4 |
| 2004/0068315 A1* | 4/2004 | Chandrasekaran et al. | 623/1.15 |
| 2004/0088043 A1* | 5/2004 | Klein | 623/1.16 |
| 2004/0143317 A1* | 7/2004 | Stinson et al. | 623/1.15 |
| 2004/0176837 A1* | 9/2004 | Atladottir et al. | 623/1.35 |
| 2004/0186554 A1* | 9/2004 | Banas et al. | 623/1.15 |
| 2004/0191404 A1* | 9/2004 | Hossainy et al. | 427/2.1 |
| 2004/0254632 A1* | 12/2004 | Alt et al. | 623/1.15 |
| 2005/0033411 A1* | 2/2005 | Wu et al. | 623/1.15 |
| 2005/0033412 A1* | 2/2005 | Wu et al. | 623/1.15 |
| 2005/0085902 A1* | 4/2005 | Wright et al. | 623/1.46 |
| 2005/0131522 A1* | 6/2005 | Stinson et al. | 623/1.15 |
| 2005/0228477 A1* | 10/2005 | Grainger et al. | 623/1.11 |
| 2006/0054604 A1* | 3/2006 | Saunders | 219/121.69 |
| 2006/0079953 A1* | 4/2006 | Gregorich et al. | 623/1.15 |
| 2006/0116751 A1* | 6/2006 | Bayle et al. | 623/1.16 |
| 2006/0129232 A1* | 6/2006 | Dicarlo et al. | 623/1.19 |
| 2006/0136041 A1* | 6/2006 | Schmid et al. | 623/1.16 |
| 2006/0136051 A1* | 6/2006 | Furst et al. | 623/1.42 |
| 2006/0177480 A1* | 8/2006 | Sung et al. | 424/426 |
| 2006/0200224 A1* | 9/2006 | Furst et al. | 623/1.15 |
| 2006/0200225 A1* | 9/2006 | Furst et al. | 623/1.15 |
| 2006/0200226 A1* | 9/2006 | Furst et al. | 623/1.15 |
| 2006/0259126 A1* | 11/2006 | Lenz | 623/1.16 |
| 2006/0264914 A1* | 11/2006 | Furst et al. | 606/1 |
| 2007/0084530 A1* | 4/2007 | Boehlert | 148/670 |

FOREIGN PATENT DOCUMENTS

| | | | | |
|---|---|---|---|---|
| WO | WO 0205863 | * | 1/2002 | A61L 31/02 |
| WO | WO 02/100298 A1 | | 12/2002 | |
| WO | WO 2004/019822 A1 | | 3/2004 | |

OTHER PUBLICATIONS

Supplementary European Search Report; May 10, 2011.

* cited by examiner

SPECIALLY CONFIGURED AND SURFACE MODIFIED MEDICAL DEVICE WITH CERTAIN DESIGN FEATURES THAT UTILIZE THE INTRINSIC PROPERTIES OF TUNGSTEN, ZIRCONIUM, TANTALUM AND/OR NIOBIUM

BACKGROUND

The present invention claims priority on PCT Application Ser. No. PCT/US2007/079119 filed Sep. 21, 2007, which in turn claims priority on U.S. Provisional Application Ser. No. 60/846,154 filed Sep. 21, 2006. The various embodiments of the present invention relate generally to medical devices, and particularly to an implant for use within a body to repair various types of body passageways, and even more particularly to an expandable graph which is useful in repairing blood vessels narrowed or occluded by disease. The medical device at least partially includes novel refractoty metals that have specific design features that accommodate the intrinsic properties of the metal.

Medical treatment of various illnesses or diseases commonly includes the use of one or more medical devices. Two types of medical devices that are commonly used to repair various types of body passageways are an expandable graft or stent, or a surgical graft. These devices have been implanted in various areas of the mammalian anatomy. One purpose of a stent is to open a blocked or partially blocked body passageway. When a stent is used in a blood vessel, the stent is used to open the occluded vessel to achieve improved blood flow which is necessary to provide for the anatomical function of an organ. The procedure of opening a blocked or partially blocked body passageway commonly includes the use of one or more stents in combination with other medical devices such as, but not limited to, an introducer sheath, a guiding catheter, a guide wire, an angioplasty balloon, etc.

Various physical attributes of a stent can contribute directly to the success rate of the device. These physical attributes include radiopacity, hoop strength, radial force, thickness of the metal, dimensions of the metal and the like. Cobalt and chromium and stainless steel are commonly used to form stents and have physical characteristics that are common throughout the design and functional phase. These materials are commonly used since such materials having a known history of safety, effectiveness, ease of manufacturing and biocompatibility.

The materials commonly used to form prior stents are biostable materials that remain in the blood vessel long after the stent has achieved its function. As such, the continued presence of the stent in the blood vessel can increase the risks associated with thrombosis, in-stent restenosis, vascular narrowing and/or restenosis in the blood vessel at the location of the stent. The presence of the stent in the blood vessel also can create a potential obstruction to later medical procedures that attempt to correct problems in a body passageway upstream from the stent. The stent can also be prone to fracturing overtime, especially when the stent is located in regions exposed to bending (e.g., leg, aims, neck, etc.). The repeated bending of the stent can eventually fatigue the stent, thereby resulting in one or more portions of the stent fracturing and/or becoming loose from the stent. These fractures (e.g., strut fractures, etc.) and/or loose portions of the stent can result in damage to the blood vessel and/or one or more regions of the vascular system down stream of the stent. The over all strut thickness also has the ability to hinder blood flow and thus remains a hindrance to healing within the mammalian anatomy.

SUMMARY OF THE INVENTION

The current invention is generally directed to a medical device that is at least partially formed of tantalum, zirconium, niobium, and/or tungsten material and a method of making the same. The medical device can also incorporate one or more specific design features and/or surface modifications that enhance one or more of the physical properties of a medical device so as to improved the success rate of such medical device and to overcome the several of the past problems associated with such medical devices.

DESCRIPTION OF DRAWINGS

Reference may now be made to the drawings which illustrate various preferred embodiments that the invention may take in physical form and in certain parts and arrangement of parts wherein.

DETAILED DESCRIPTION OF INVENTION

Figure 1:
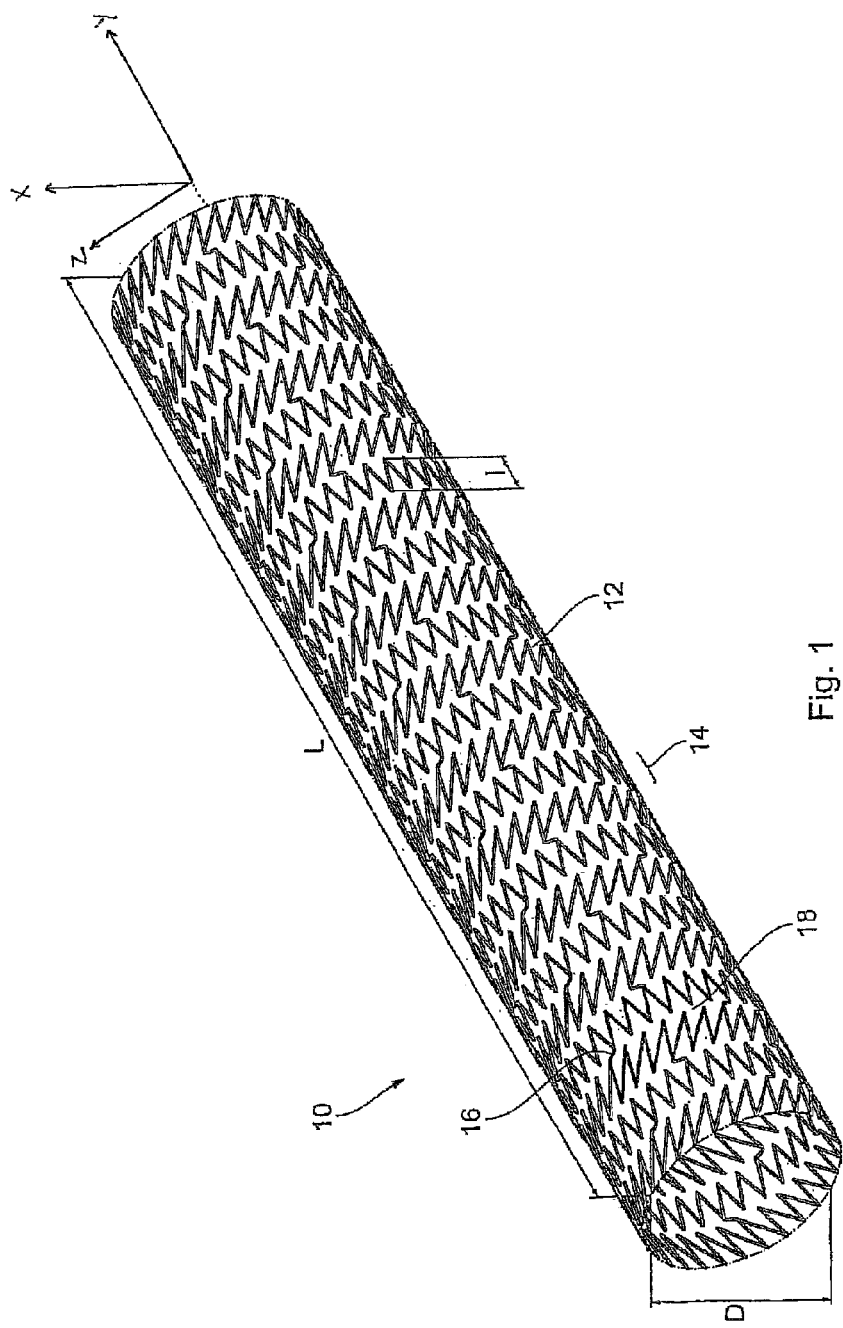
FIG. 1 is an front elevation view of a stent in accordance with the present invention.

The previously mentioned shortcomings of prior art medical devices are addressed by the novel medical device of the present invention. The medical device in accordance with one present embodiment can be in the form of many different medical devices such as, but are not limited to, stents, grafts, surgical grafts (e.g., vascular grafts, etc.), orthopedic implants, staples, sheaths, guide wires, balloon catheters, hypotubes, catheters, electrophysiology catheters, cutting devices, etc.

In one non-limiting aspect, the medical device is directed for use in a body passageway. As used herein, the term "body passageway" is defined to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). The techniques employed to deliver the medical device to a treatment area include, but are not limited to, angioplasty, vascular anastomoses, transplantation, implantation, subcutaneous introduction, minimally invasive surgical procedures, interventional procedures, and any combinations thereof For vascular applications, the term "body passageway" primarily refers to blood vessels and chambers in the heart. The blood vessels can be located in any portion of the body (e.g., legs, arms, brain, body organs, etc.).

In one non-limiting embodiment, the medical device is in the form of a stent. The stent can be an expandable stent that is expandable by a balloon and/or other means. The stent can have many shapes and forms. Such shapes can include, but are not limited to, stents disclosed in U.S. Pat. Nos. 6,206,916 and 6,436,133; and all the prior art cited in these patents. These various designs and configurations of stents in such patents are incorporated herein by reference. When the medical device is in the form of a stent, the stent is designed to be insertable into a treatment area (e.g., body passageway, etc.) and be expanded in the treatment area to enable better or proper fluid flow through the body passageway.

In most cases, such as intraluminal endoprostheses, a durable support function afforded by the endoprosthesis is required. In some situations, the body tissue can recover in a more efficient manner in the presence of the support prosthesis that has a specific design feature and is comprised of a refractory metal that has minimized content of metal and still exemplifies the mechanical characteristics required for the advanced healing of such mammalian anatomy. In view of this realization, the present invention is directed to a medical device that is at least partially form of a zirconium, tantalum, niobium and/or tungsten material. The present embodiments are in part directed to the formation of medical devices for use in such situations.

Traditional metals have a finite thickness that makes them functional. If the thickness is reduced below a certain point, the medical devices become unstable and incapable of functioning without fracturing. The converse is also true, especially with drug and polymer coatings over the metal adding to the thickness of the stent or other medical device. That is, the device may become too bulky due to the thickness of the metal and any coatings, thus limiting its expandability and profile, resulting in undue blockages in the blood vessel. With new manufacturing techniques and new metals, the device can be reduced in thickness without the threat of fracturing, compared to traditional metals. A drug and/or polymer coating can then be applied to the device at even greater thicknesses than previously, while still not approaching the upper limit of thickness that would cause device failure as described above.

Thus, in one non-limiting embodiment, the medical device can be formed of a material that is considered a refractory metal and at least partially includes zirconium, tantalum, tungsten and/or niobium. By utilizing the intrinsic properties of one or more of these materials, a medical device such as, but not limited to a stent, can be manufactured in such a way that has not been previously produced, and which can at least partially overcome potential problems with thrombosis, in-stent restenosis, vascular narrowing and/or restenosis in the body passageway in and/or around at the treatment location of the stent. In order to achieve the desired mechanical properties of one or more of these metals, the medical device typically should include one or more specific design features. Stainless steel and cobalt and chromium have only a limited potential when used in medical device and such limited potential cannot be enhanced due to their physical properties.

In another and/or additional non-limiting aspect, the medical device that is at least partially made of zirconium, tantalum, niobium and/or tungsten has improved physical properties as compared to past medical devices. The metal used to at least partially form the medical device can be radiopaque; however, this is not required. In another and/or additional one non-limiting embodiment, the metal used to at least partially form the medical device can improve one or more physical properties of such medical device (strength, durability, hardness, biostability, bendability, coefficient of friction, radial strength, flexibility.tensile strength, tensile elongation, longitudinal lengthening, stress-strain properties, improved recoil properties, radiopacity, heat sensitivity, biocompatibility, etc.); however, this is not required. These one or more improved physical properties of the metal used in the medical device can be achieved in the medical device without having to increase the bulk, volume and/or weight of the medical device, and in some instances these improved physical properties can be obtained even when the volume, bulk and/or weight of the medical device is reduced as compared to medical devices that are at least partially formed from traditional stainless steel or cobalt and chromium alloy materials; however, this is not required.

In still another and/or additional one non-limiting embodiment, the medical device comprises a metal or alloy, that, compared to traditional stainless steel or cobalt chromium alloy materials, can 1) increase the radiopacity of the medical device, 2) increase the radial strength of the medical device, 3) increase the yield strength and/or ultimate tensile strength of the medical device, 4) improve the stress-strain properties of the medical device, 5) improve the crimping and/or expansion properties of the medical device, 6) improve the bendability and/or flexibility of the medical device, 7) improve the strength and/or durability of the medical device, 8) increase the hardness of the medical device, 9) improve the longitudinal lengthening properties of the medical device, 10) improved the recoil properties of the medical device, 11) improve the friction coefficient of the medical device, 12) improve the heat sensitivity properties of the medical device, 13) improve the biostability and/or biocompatibility properties of the medical device, and/or 14) enable smaller, thinner and/or lighter weight medical devices to be made.

In still another and/or additional non-limiting aspect, the present medical device generally includes one or more materials that impart the desired properties to the medical device so as to withstand the manufacturing processes that is needed to produce the medical device. These manufacturing processes can include, but are not limited to, laser cutting, etching, crimping, annealing, drawing, pilgering, electroplating, electro-polishing, chemical polishing, cleaning, pickling, ion beam deposition or implantation, sputter coating, vacuum deposition, etc.

In yet another and/or additional non-limiting aspect, the design characteristics of the medical device are developed into an array of configurations that do not adversely affect the function of such medical device. That is, besides the desired mechanical properties of the medical device (e.g., stent, etc.), the medical device is designed to interact with the body tissue at the implantation location in a manner such that renewed vessel constrictions do not occur, in particular vessel constrictions caused by the medical device itself. Re-stenosis (re-constriction of the vessel) should be avoided as much as possible. It is also desirable that the medical device, as far as possible, is responsible for little or no inflammatory effect at the implantation site. In regard to a metal medical device, it is moreover desirable if the composition products of the medical device have little or no negative physiological effects. As can be appreciated, the composition of the products of the medical device can have positive physiological effects; however, this is not required.

In still yet another and/or additional non-limiting aspect, the design of the medical device can take any number of different structures. Thus, with reference to FIG. 1, there is shown an exemplary embodiment endoluminal prosthesis in the form of a stent 10 having a carrier structure. As can be appreciated, the stent can have many other or additional configurations. As illustrated in FIG. 1, the stent 10 and its carrier structure are in the form of a hollow body which is open at its ends and the peripheral wall of which is formed by the carrier structure which in turn is formed by partially folded legs 12. The legs 12 form support portions 14 which are each formed by a leg 12 which is closed in an annular configuration in the longitudinal direction and which is folded in a zig-zag or meander-shaped configuration. The stent is suitable for coronary use or other types of use.

The carrier structure of the stent 10 is formed by a plurality of such support portions 12 which occur in succession in the longitudinal direction. The support portions 12 are connected together by way of one or more connecting legs 16. As illustrated in FIG. 1, each two connecting legs 16 are mutually adjacent in the peripheral direction and the parts of the support portions 12, which are in mutually opposite relationship between those connecting legs 16, define a mesh 18 of the stent 10. As can be appreciated, the legs can be oriented in many different configurations. Each mesh 18 encloses a radial opening in the peripheral wall or the carrier structure of the stent 10.

The stent 10 is expandable in the peripheral direction by virtue of the folding of the support portions 12. That is affected for example, by means of a per se known balloon catheter which at its distal end, has a balloon which is expandable by means of a fluid. The stent 10 is crimped onto the deflated balloon, in the compressed condition. Upon expansion of the balloon, both the balloon and also the stent 10 are enlarged. The balloon can then be deflated again and the stent 10 is released from the balloon. In that way, the catheter can serve simultaneously for introducing the stent 10 into a blood vessel and in particular into a constricted coronary vessel and also for expanding the stent 10 at that location.

Figure 2:
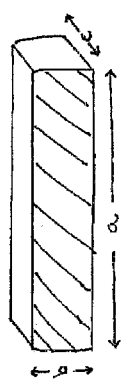
FIG. 2 is an enlarged sectional view of a strut of the stent illustrated in FIG. 1.
Figure 3:
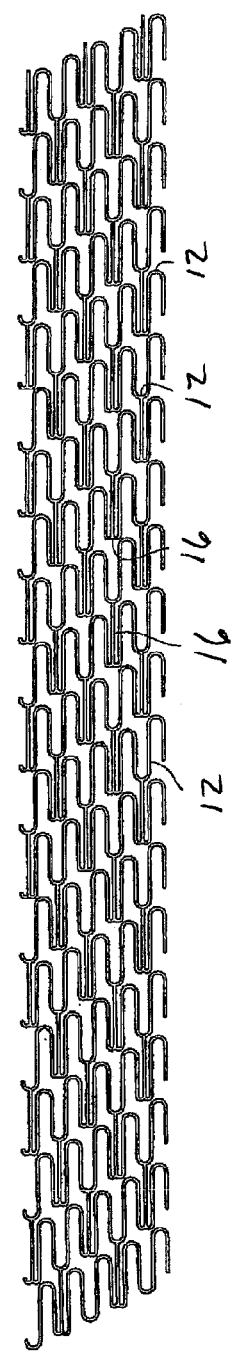
FIG. 3 is a side view of a portion of a stent body in accordance with one aspect of the invention.
Figure 4:
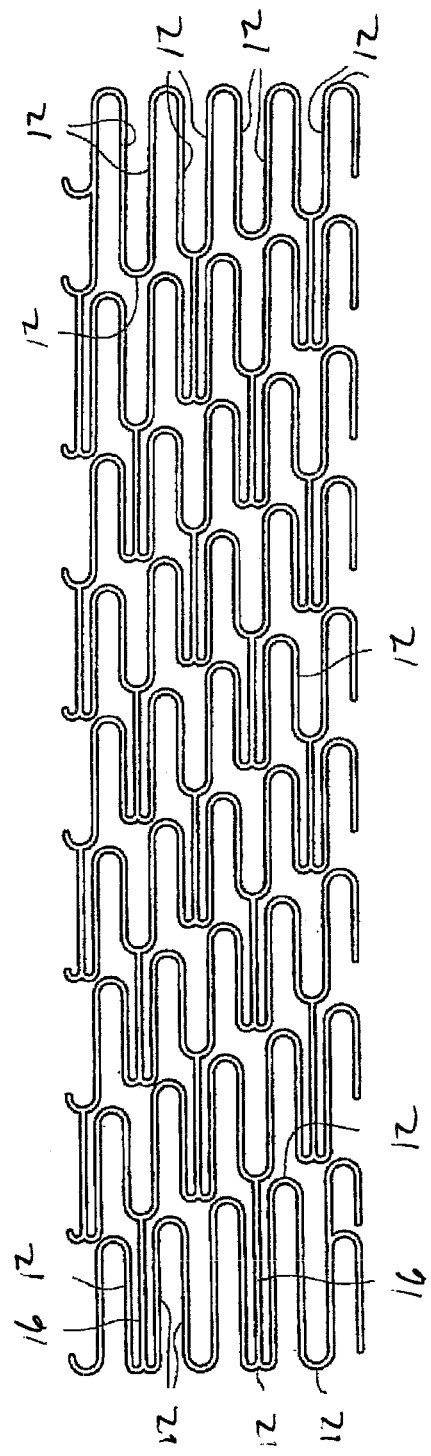
FIG. 4 is a side view of another configuration of a stent.
Figure 5:
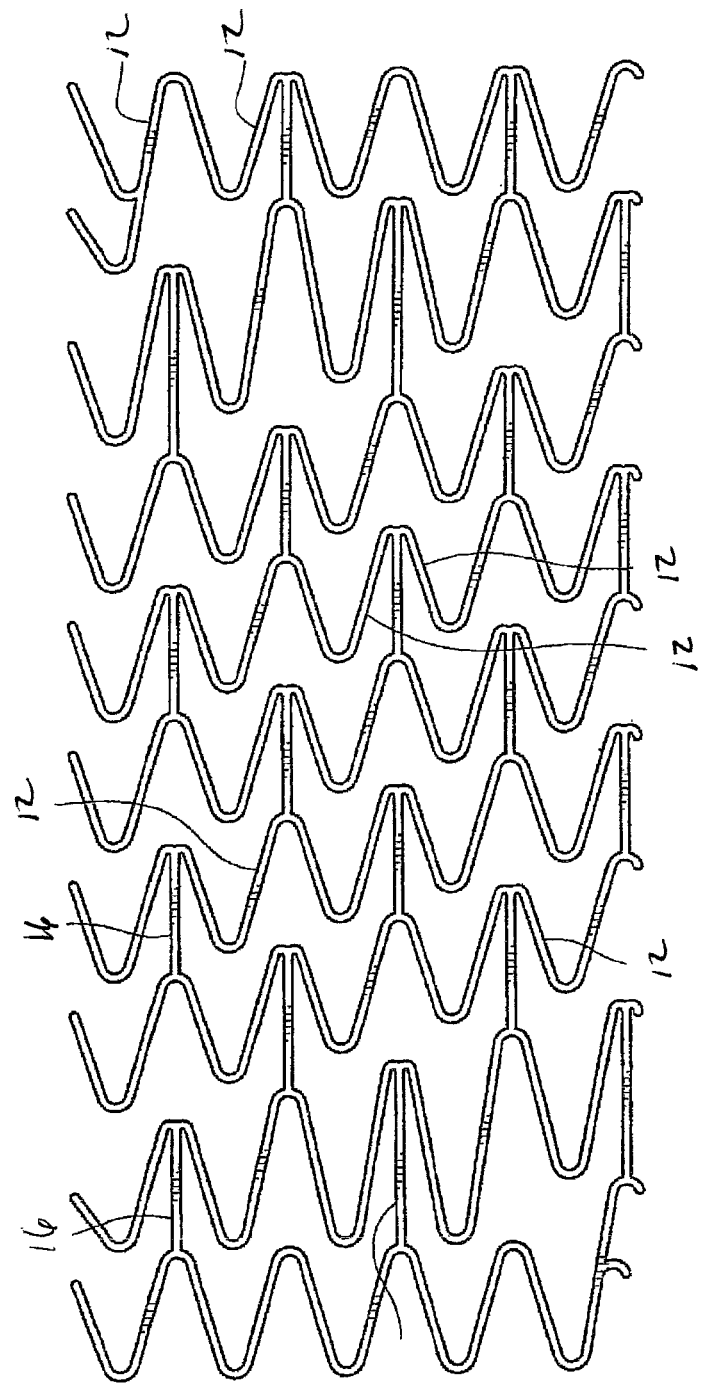
FIG. 5 is a side view of yet another configuration of a stent.
Figure 6:
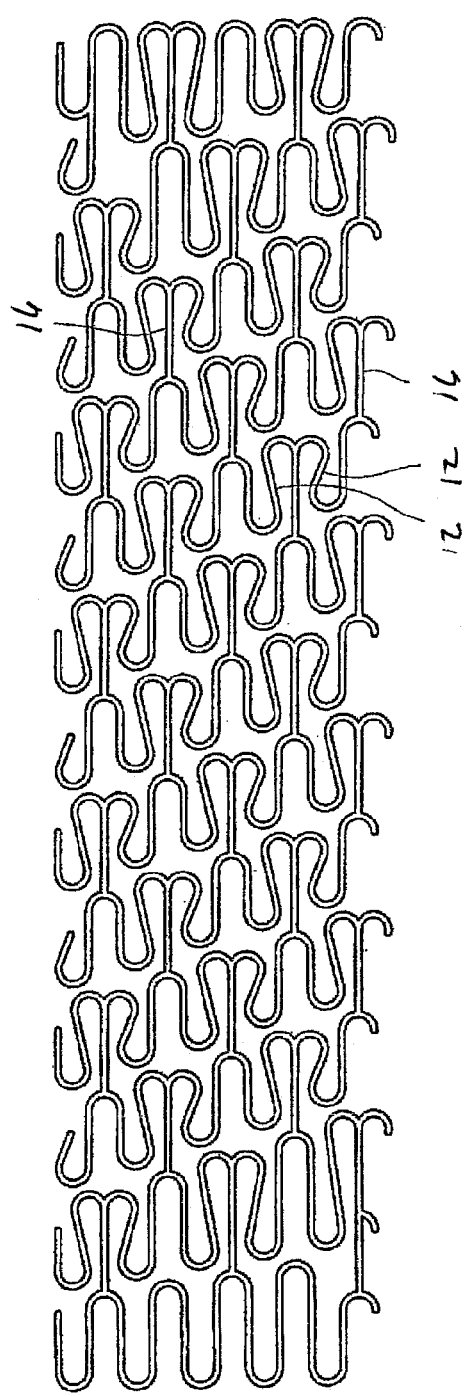
FIG. 6 is yet another stent configuration according to the present invention.

The geometry of the peripheral wall and legs of the stent will be described by using the co-ordinates shown in FIG. 1, more specifically x as the longitudinal axis of the stent, y as coordinates extending radially in the peripheral direction of the stent with respect to the longitudinal direction x, and z as coordinates extending along the width or thickness of the stent. It can be seen from the view in cross-section through a support portion as illustrated in FIG. 2 that the geometry can be described by a length a, a width b, and a thickness c. In this case, the length a is the dimension of a bar in the longitudinal direction x with respect to the stent while the width b represents the dimension of a bar in the direction of a peripheral surface formed by the peripheral wall of the stent, and the thickness c is the dimension extending into the interior volume of the stent.

In another and/or additional non-limiting aspect of the present invention, the wall thickness of at least a portion of the support portions and/or connecting legs of the stent vary over the length and/or over the periphery of the stent along at least one of the axes x, y, and z. The varying of the thickness of the support portions and/or connecting legs enables the stent to be controllably expanded in a body passageway. The stent can be designed so that the entire stent expands uniformly, or be designed such that one or more portions of the stent expands at differing times and/or rates from one or more other portions of the stent. That is, at least one of the dimensions a, b and c of at least some of the support portions and/or connecting legs in the stent can be varied.

Figure 10:
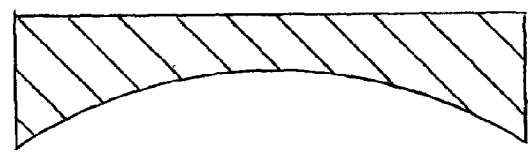
FIG. 10 is a stent portion showing variations in thickness over its length in accordance with another embodiment.

In still another and/or additional non-limiting aspect of the present invention, the stent is designed such that the first and last thirds of the stent with support portion and/or connecting legs wall have thicknesses a and/or widths b that are slightly greater than the thicknesses of the configurations in the middle third of the stent. In this non-limiting configuration, the stent design accounts for the first and last thirds being subjected to more turbulence and other degrading influences than the middle third. Alternately, the wall thickness of one or more portions of the stent can be steadily varied over the length of a support portion and/or a connecting leg as shown in FIG. 10. In FIG. 10, the wall thickness is at a minimum in the middle of the support portion and/or a connecting leg and at a maximum on the two ends. As can be appreciated, other non-limiting examples of varying wall thickness configurations can be used on the legs and/or support portions (e.g., notches in the legs/support portion, ribs in the legs/support portion, etc.).

In yet another and/or additional non-limiting aspect, the exact thickness and/or width variations along the longitudinal axis of the stent will in part depend on the material used to construct the stent as well as the design of the support portions and/or connecting legs of the stent. In addition, the use of polymer coatings (as detailed below) as well as other layers added to the stent surface can be used to affect one or more properties of the stent. These properties of the stent can thus be used to control the degradation rate and/or release rate of one or more of the polymer and/or drugs on the stent. In one non-limiting one embodiment, the thickness of the support portions and/or connecting legs of the stent is generally about 0.002-0.006 inch. As can be appreciated, one or more portions of the support portion and/or connecting leg can have greater or small thickness. For example, the average thickness of one or more legs can be about 0.0042 inch; however, the thinnest portion of the one or more legs could be about 0.0012-0.0035 inch and/or the thickest portion of the one or more legs could be about 0.0045-0.007 inch.

As discussed above, the thickness of the material in one portion of the stent can be different from the thickness of another material in another portion of the stent, so as to achieve the desired rate of structural success of the stent in one or more portions of the stent.

In still yet another and/or additional non-limiting aspect, the shape of the support portions and/or connecting legs of the stent can be selected to increase or decrease the strength of one or more portions of the support portions and/or connecting legs. As such pits, jagged surfaces, sharp angles, etc. can be incorporated into the stent design to alter the strength and/or flexibility of one or more portions of the stent. As can also be appreciated, smooth surfaces, curved surfaces, etc. can be used. As such, the structural configuration of the stent can also or alternatively be used to achieve the desired rate of success of the stent.

Figure 7A:
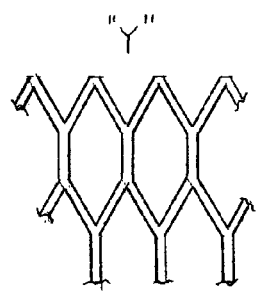
FIG. 7A-K are various possible configurations for support portions of a stent in accordance with another embodiment.
Figure 7B:
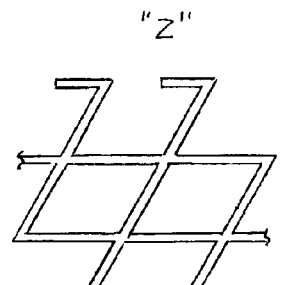
Figure 7C:
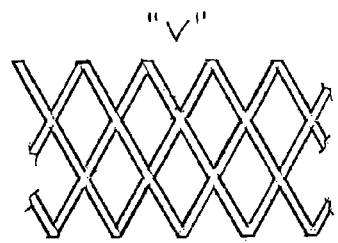
Figure 7D:
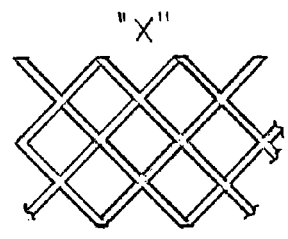
Figure 7E:
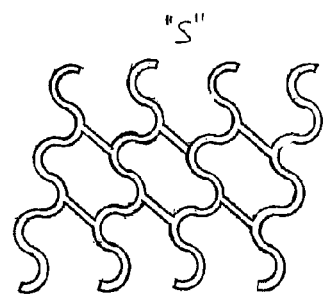
Figure 7F:
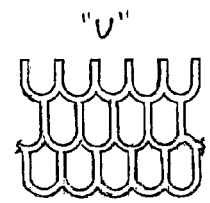
Figure 7G:
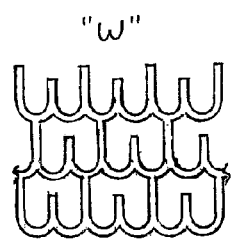
Figure 7H:
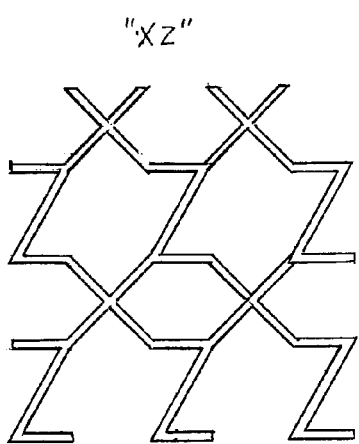
Figure 7I:
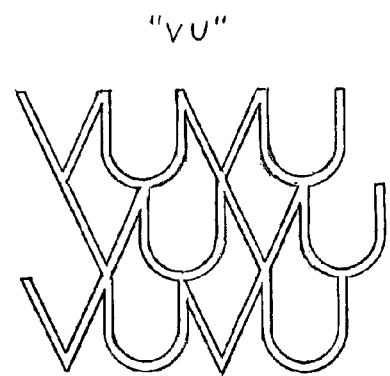
Figure 7J:
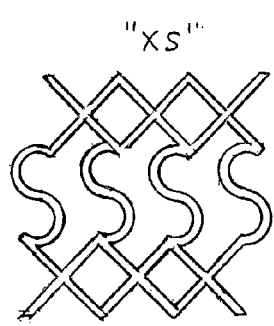
Figure 7K:
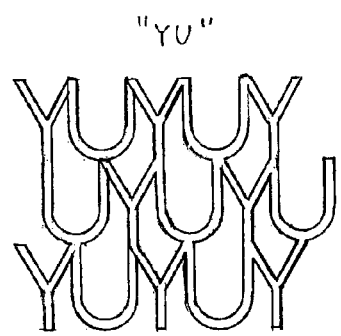

In another and/or additional non-limiting aspect, many configurations for the support portions and/or connecting legs of the stent lattice are possible. In various possible non-limiting embodiments, the configurations for the support portions can take multiple forms, including, e.g., the shape of a "W","Y","Z", "X", "U", "V" and/or "S". Stent structures showing these configurations are shown in FIGS. 7A-7G. These configurations also can have straight line or other structured connecting legs that connect the previously mentioned configurations, such as seen in FIG. 7E showing straight line connecting legs between "S" configurations. In addition, an almost limitless variety of other configurations can be achieved by combining one or more of the above basic configurations. Some non-limiting examples of configurations using two combined basic configurations are shown in FIGS. 7H-7K, which show "XZ", "VU", "XS", and "YU" configurations. Many more such combinations are possible. Still additional configurations can be seen in FIGS. 3-6 and 12. All of these connectors and configurations can have multiple thicknesses along its axis and have different angles or degrees of separation. This is utilized to accommodate the different stress points that occur so as not to weaken the device prior to achieving its' goal of repairing or supporting a mammalian organ or vessel.

In still another and/or additional non-limiting aspect, the medical device such as a stent can be fully or partially formed of a metal or a metal alloy. Hereinafter, descriptions using the term "alloy" may be used to generally describe embodiments using both a pure metal as well as an alloy of different metals. In one non-limiting embodiment, the medical device is generally designed to include at least about 25 weight percent of the metal alloy; however, this is not required. In one non-limiting embodiment, the medical device includes at least about 40 weight percent of the metal alloy. In another and/or additional non-limiting embodiment, the medical device includes at least about 50 weight percent of the metal alloy. In still another and/or additional non-limiting embodiment, the medical device includes at least about 60 weight percent of the metal alloy. In yet another and/or additional non-limiting embodiment, the medical includes at least about 70 weight percent of the metal alloy. In still yet another and/or additional non-limiting embodiment, the medical includes at least about 85 weight percent of the metal alloy. In another and/or additional non-limiting embodiment, the medical device includes at least about 90 weight percent of the metal alloy. In still another and/or additional non-limiting embodiment, the medical device includes at least about 95 weight percent of the metal alloy. In yet another and/or additional non-limiting embodiment, the medical device includes about 100 weight percent of the metal alloy.

In another and/or additional non-limiting aspect, the metal alloy that is used to form all or part of the medical device 1) is not clad, metal sprayed, plated and/or formed (e.g., cold worked, hot worked, etc.) onto another metal, or 2) does not have another metal or metal alloy metal sprayed, plated, clad and/or formed onto the novel metal alloy. It will be appreciated that in some applications, the metal alloy for use in the present devices may be clad, metal sprayed, plated and/or formed onto another metal, or another metal or metal alloy may be plated, metal sprayed, clad and/or formed onto the metal alloy when forming all or a portion of the medical device.

In yet another and/or additional non-limiting aspect, the metal alloy that is used to form all or a portion of the medical device includes a majority weight percent of tantalum. A minority weight percent of tungsten may form part of the alloy. In one non-limiting embodiment, the metal alloy comprises about 7.0-10.0% by weight tungsten and 90.0-93.0% tantalum. Specific non-limiting contemplated metal alloys in accordance with the present invention comprise 1) 92.5% tantalum with 7.5% tungsten, 2) 90% tantalum with 10% tungsten, and 3) 90-97.5% tantalum and 2.5-10% tungsten. Other non-limiting contemplated metal alloys in accordance with the present invention can include niobium and/or zirconium. In yet another and/or additional non-limiting embodiment, the metal comprises niobium. In one embodiment, the metal comprises at least about 95% niobium, and more particularly about 99.5-100% niobium. In a second embodiment, the metal comprises an alloy of niobium and zirconium wherein niobium has a larger weight percent than zirconium.

In still yet another and/or additional non-limiting aspect of the present invention, the medical device that is at least partially formed from the metal alloy can be formed by a variety of manufacturing techniques. In one non-limiting embodiment of the invention, the medical device can be formed from a rod or tube of the metal alloy. If a solid rod of the metal alloy is formed, the rod can be drilled (e.g., gun drilled, EDM, etc.) to form a cavity or passageway partially or fully through the rod; however, this is not required. The rod or tube can be cleaned, polished, annealed, drawn, etc. to obtain the desired diameter and/or wall thickness of the metal rod or tube. After the metal rod or tube has been formed to the desired diameter and wall thickness, the metal tube can further processed by one or more processing techniques such as, but not limited to, laser cutting, etching, etc. After the medical device has been formed, the medical device can be cleaned, polished, sterilized, etc.

In another and/or additional non-limiting aspect of the present embodiments, the medical device can be in the form of a stent. The stent can have a variety of applications such as, but not limited to placement into the vascular system, esophagus, trachea, colon, biliary tract, or urinary tract; however, the stent can have other applications. The stent can have one or more body members, wherein each body member includes first and second ends and a wall surface disposed between the first and second ends. Each body member can have a first cross-sectional area which permits delivery of the body member into a body passageway, and a second, expanded cross-sectional area.

The expansion of the stent body member can be accomplished in a variety of manners. Typically, the body member is expanded to its second cross-sectional area by a radially, outwardly extending force applied at least partially from the interior region of the body member (e.g., by use of a balloon, etc.); however, this is not required. When the second cross-sectional area is variable, the second cross-sectional area is typically dependent upon the amount of radially outward force applied to the body member. The stent can be designed such that the body member expands while retaining the original length of the body member; however, this is not required. The body member can have a first cross-sectional shape that is generally circular so as to form a substantially tubular body member; however, the body member can have other cross-sectional shapes. When the stent includes two of more body members, the two of more body members can be connected together by at least one connector member.

The stent can include rounded, smooth and/or blunt surfaces to minimize and/or prevent damage to a body passageway as the stent is inserted into a body passageway and/or expanded in a body passageway; however, this is not required. The stent can also have its subsurface treated in such a way that it forms gaps below the surface that are sponge-like; however, this is not required. The stent can be treated with gamma, beta and/or e-beam radiation, and/or otherwise sterilized; however, this is not required. The stent can have multiple sections; however, this is not required. The sections of the stent can have a uniform architectural configuration, or can have differing architectural configurations. Each of the sections of the stent can be formed of a single part or formed of multiple parts which have been attached. When a section is formed of multiple parts, typically the section is formed into one continuous piece; however, this is not required.

In still another and/or additional non-limiting aspect of the present invention, one or more portions of the medical device can include, contain and/or be coated with one or more biological agents that are used to facilitate in the success of the medical device and/or treated area. The medical device can include, contain and/or be coated with one or more biological agents. The term "biological agent" includes, but is not limited to, a substance, drug or otherwise formulated and/or designed to prevent, inhibit and/or treat one or more biological problems, and/or to promote the healing in a treated area. Non-limiting examples of biological problems that can be addressed by one or more biological agents include, but are not limited to, viral, fungus and/or bacteria infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; and/or the like.

Non-limiting examples of biological agents that can be used include, but are not limited to, 5-Fluorouracil and/or derivatives thereof; 5-Phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular $Ca_{2+}$ transport such as L-type (e.g., diltiazem, nifedipine, verapamil, etc.) or T-type $Ca_{2+}$ channel blockers (e.g., amiloride, etc.); alpha-adrenergic blocking agents and/or derivatives thereof; alteplase and/or derivatives thereof; amino glycosides and/or derivatives thereof (e.g., gentamycin, tobramycin, etc.); angiopeptin and/or derivatives thereof; angiostatic steroid and/or derivatives thereof; angiotensin II receptor antagonists and/or derivatives thereof; anistreplase and/or derivatives thereof; antagonists of vascular epithelial growth factor and/or derivatives thereof; anti-biotics; anti-coagulant compounds and/or derivatives thereof; anti-fibrosis compounds and/or derivatives thereof; anti-fungal compounds and/or derivatives thereof; anti-inflammatory compounds and/or derivatives thereof; Anti-Invasive Factor and/or derivatives thereof; anti-metabolite compounds and/or derivatives thereof (e.g., staurosporin, trichothecenes, and modified diphtheria and ricin toxins, Pseudomonas exotoxin, etc.); anti-matrix compounds and/or derivatives thereof (e.g., colchicine, tamoxifen, etc.); antimicrobial agents and/or derivatives thereof; anti-migratory agents and/or derivatives thereof (e.g., caffeic acid derivatives, nilvadipine, etc.); anti-mitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, $Ca_{2+}$/calmodulin kinase II, casein kinase II, etc.); aspirin and/or derivatives thereof; azathioprine and/or derivatives thereof; i-Estradiol and/or derivatives thereof; α-i-anticollagenase and/or derivatives thereof; calcium channel blockers and/or derivatives thereof; calmodulin antagonists and/or derivatives thereof (e.g., H7, etc.); CAPTOPRIL and/or derivatives thereof; cartilage-derived inhibitor and/or derivatives thereof; CHlMP-3 and/or derivatives thereof; cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamocifen, etc.); chymostatin and/or derivatives thereof; CILAZAPRIL and/or derivatives thereof; clopidigrel and/or derivatives thereof; clotrimazole and/or derivatives thereof; colchicine and/or derivatives thereof; cortisone and/or derivatives thereof; Coumadin and/or derivatives thereof; curacin-A and/or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and/or derivatives thereof; desirudin and/or derivatives thereof; dexamethazone and/or derivatives thereof; dipyridamole and/or derivatives thereof; eminase and/or derivatives thereof; endothelin and/or derivatives thereof; endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g., dexamethasone, betamethasone, etc.); glycoprotein llb/llla platelet membrane receptor antibody and/or derivatives thereof; GM-CSF and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and/or derivatives thereof; hyaluronate and/or derivatives thereof; hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium/calcium antiporter and/or derivatives thereof (e.g., amiloride, etc.); inhibitors of the $IP_3$ receptor and/or derivatives thereof; inhibitors of the sodium/hydrogen antiporter and/or derivatives thereof (e.g., amiloride and derivatives thereof, etc.); insulin and/or derivatives thereof; Interferon alpha 2 Macroglobulin and/or derivatives thereof; ketoconazole and/or derivatives thereof; Lepirudin and/or derivatives thereof; LISINOPRIL and/or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof; monoclonal antibodies and/or derivatives thereof; mutamycin and/or derivatives thereof; naproxen and/or derivatives thereof; nitric oxide and/or derivatives thereof; nitroprusside and/or derivatives thereof; nucleic acid analogues and/or derivatives thereof (e.g., peptide nucleic acids, etc.); nystatin and/or derivatives thereof; oligonucleotides and/or derivatives thereof; paclitaxel and/or derivatives thereof; penicillin and/or derivatives thereof; pentamidine isethionate and/or derivatives thereof; phenindione and/or derivatives thereof; phenylbutazone and/or derivatives thereof; phosphodiesterase inhibitors and/or derivatives thereof; Plasminogen Activator Inhibitor-1 and/or derivatives thereof; Plasminogen Activator Inhibitor-2 and/or derivatives thereof; Platelet Factor 4 and/or derivatives thereof; platelet derived growth factor and/or derivatives thereof; plavix and/or derivatives thereof; POSTMI 75 and/or derivatives thereof; prednisone and/or derivatives thereof; prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, in-111, 1-123, 1-125, 1-131, Re-186, Re-188, Au-198, Au-199, Pb-203, At-211, Pb-212, Bi-212, $H_3P^{32}O_4$, etc.); rapamycin and/or derivatives thereof; receptor antagonists for histamine and/or derivatives thereof; refludan and/or derivatives thereof; retinoic acids and/or derivatives thereof; revasc and/or derivatives thereof; rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and/or derivatives thereof; THi and/or derivatives thereof (e.g., Interleukins-2, -12, and -15, gamma interferon, etc.); thioprotese inhibitors and/or derivatives thereof; taxol and/or derivatives thereof (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anticoagulant peptide and/or derivatives thereof; thioprotese inhibitors and/or derivatives thereof; thyroid hormone and/or derivatives thereof; Tissue Inhibitor of Metalloproteinase-1 and/or derivatives thereof; Tissue Inhibitor of Metalloproteinase-2 and/or derivatives thereof; tissue plasma activators; TNF and/or derivatives thereof; tocopherol and/or derivatives thereof; toxins and/or derivatives thereof; tranilast and/or derivatives thereof; transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the biological agent can include one or more derivatives of the above listed compounds and/or other compounds.

In one non-limiting example, the medical device can be coated with and/or includes one or more biological agents such as, but not limited to, trapidil and/or trapidil derivatives, taxol, taxol derivatives (e.g., taxotere, baccatin, 10-deacetyl-taxol, 7-xylosyl-IO-deacetyltaxol, cephalomannine, 10-deacetyl-7-epitaxol, 7 epitaxol, 10-deacetylbaccatin III, 10-deacetylcephaolmannine, etc.), cytochalasin, cytochalasin derivatives (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.), paclitaxel, paclitaxel derivatives, rapamycin, rapamycin derivatives, 5-Phenylmethimazole, 5-Phenylmethimazole derivatives, GM-CSF (granulo-cyte-macrophage colony-stimulating-factor), GM-CSF derivatives, or combinations thereof. In one non-limiting embodiment of the invention, the medical device can be partially of fully coated with one or more biological agents, impregnated with one or more biological agents to facilitate in the success of a particular medical procedure.

In another and/or additional non-limiting aspect of the present invention, the one or more biological agents can be coated on the medical device by a variety of mechanisms such as, but not limited to, spraying (e.g., atomizing spray techniques, etc.), dip coating, roll coating, sonication, brushing, plasma deposition, depositing by vapor deposition. In another and/or alternative non-limiting embodiment of the invention, the type and/or amount of biological agent included on, in and/or in conjunction with the medical device is generally selected for the treatment of one or more medical treatments. Typically the amount of biological agent included on, in and/or used in conjunction with the medical device is about 0.01-100 µg per mm². However, other amounts can be used.

In still another and/or additional non-limiting aspect of the present invention, the amount of two of more biological agents on, in and/or used in conjunction with the medical device can be the same or different. For instance, one or more biological agents can be coated on one or more portions of the medical device to provide local and/or systemic delivery of one or more biological agents in and/or to a body passageway to a) inhibit or prevent thrombosis, in-stent restenosis, vascular narrowing and/or restenosis after the medical device has been inserted in and/or connected to a body passageway, b) at least partially passivate, remove and/or dissolve lipids, fibroblast, fibrin, etc. in a body passageway so as to at least partially remove such materials and/or to passivate such vulnerable materials (e.g., vulnerable plaque, etc.) in the body passageway in the region of the medical device and/or down stream of the medical device. As can be appreciated, the one or more biological agents can have many other or additional uses.

In yet another and/or additional non-limiting example, the medical device is coated with and/or includes one or more biological agents such as, but not limited to trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof, and one or more additional biological agents, such as, but not limited to, biological agents associated with thrombolytics, vasodilators, anti-hypertensive agents, anti-microbial or anti-biotic, anti-mitotic, anti-proliferative, anti-secretory agents, non-steroidal antiinflammatory drugs, immunosuppressive agents, growth factors and growth factor antagonists, antitumor and/or chemotherapeutic agents, anti-polymerases, antiviral agents, anti-body targeted therapy agents, hormones, anti-oxidants, biologic components, radio-therapeutic agents, radiopaque agents and/or radio-labeled agents. In addition to these biological agents, the medical device can be coated with and/or include one or more biological agents that are capable of inhibiting or preventing any adverse biological response by and/or to the medical device that could possibly lead to device failure and/or an adverse reaction by human or animal tissue. A wide range of biological agents thus can be used.

In another and/or additional non-limiting aspect of the present invention, the one or more biological agents on and/or in the medical device, when used on the medical device, can be released in a controlled manner so the area in question to be treated is provided with the desired dosage of biological agent over a sustained period of time. As can be appreciated, controlled release of one or more biological agents on the medical device is not always required and/or desirable. As such, one or more of the biological agents on and/or in the medical device can be uncontrollably released from the medical device during and/or after insertion of the medical device in the treatment area.

It can also be appreciated that one or more biological agents on and/or in the medical device can be controllably released from the medical device and one or more biological agents on and/or in the medical device can be uncontrollably released from the medical device. As such, the medical device can be designed such that 1) all the biological agent on and/or in the medical device is controllably released, 2) some of the biological agent on and/or in the medical device is controllably released and some of the biological agent on the medical device is non-controllably released, or 3) none of the biological agent on and/or in the medical device is controllably released. The medical device can also be designed such that the rate of release of the one or more biological agents from the medical device is the same or different. The medical device can also be designed such that the rate of release of the one or more biological agents from one or more regions on the medical device is the same or different.

In still another and/or additional non-limiting aspect of the present invention, non-limiting arrangements that can be used to control the release of one or more biological agent from the medical device, when such controlled release is desired, include a) at least partially coat one or more biological agents with one or more polymers, b) at least partially incorporate and/or at least partially encapsulate one or more biological agents into and/or with one or more polymers, and/or c) insert one or more biological agents in pores, passageway, cavities, etc. in the medical device and at least partially coat or cover such pores, passageway, cavities, etc. with one or more polymers. As can be appreciated, other or additional arrangements can be used to control the release of one or more biological agent from the medical device.

In yet another and/or additional non-limiting aspect of the present invention, one or more polymers can be used to at least partially control the release of one or more biological agent from the medical device. The one or more polymers, when used, can be porous or non-porous. As such, the one or more biological agents on the medical device can be 1) coated on one or more surface regions of the medical device, and/or 2) form at least a portion or be included in at least a portion of the structure of the medical device. When the one or more biological agents are coated on the medical device, the one or more biological agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials.

Figure 11A:
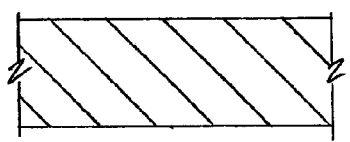
FIG. 11A-11F show various coating combinations that can be used on the stents of the present invention.
Figure 11B:
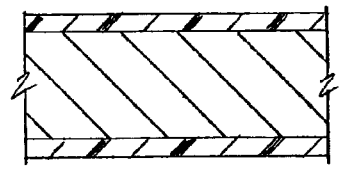
Figure 11C:
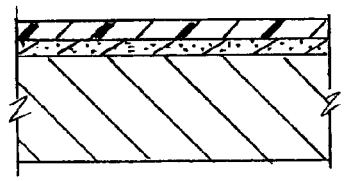
Figure 11D:
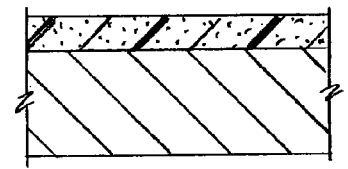
Figure 11E:
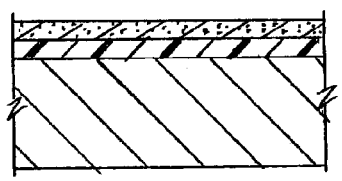
Figure 11F:
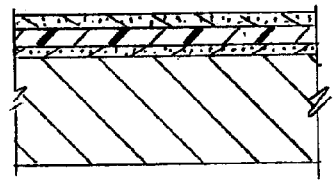
Figure 12:
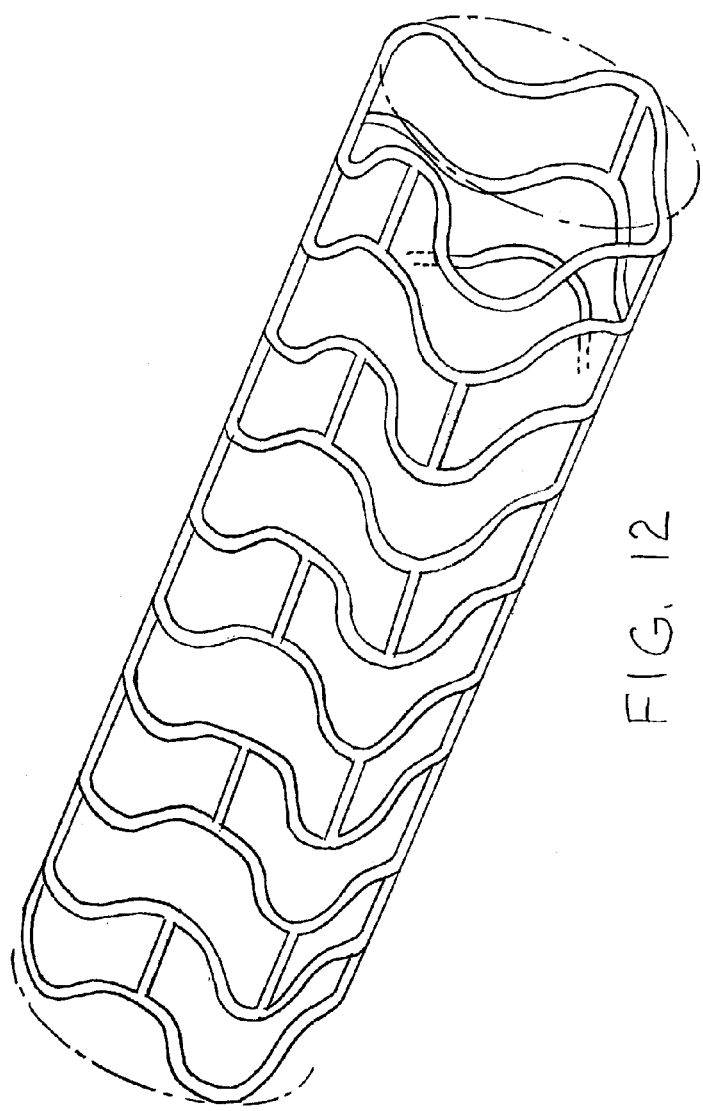
FIG. 12 shows yet another possible stent configuration according to another embodiment.

With reference to FIGS. 11A-11F, various non-limiting arrangements for the coating of polymer and/or biological agents on the surfaces of the medical device are shown. As can be appreciated, many other coating combinations and configurations can be used. FIG. 11A shows a non-coated body portion. FIG. 11B shows a body portion coated on all sides with a biological agent. FIG. 11C shows a body portion coated with a polymer, which is then coated with a biological agent. FIG. 11D shows a body portion coated with an intimate mixture of biological agent and polymer. FIG. 11E shows a body portion coated with biological agent, which is then coated with a polymer. FIG. 11F shows a body portion with a sandwich layer coating of biological agent between two layers of polymer.

Figure 8:
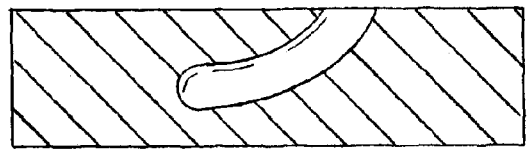
FIG. 8 is a stent having a cavity in accordance with one embodiment.
Figure 9A:
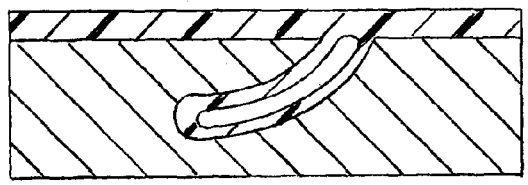
FIG. 9A-9B show the stent cavity filled with various coatings.
Figure 9B:
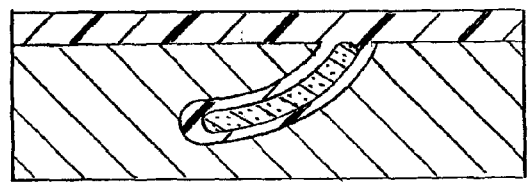

In still yet another and/or additional non-limiting aspect of the present invention, one or more portions of a support portion and/or a connecting leg of the stent can include one or more passageways. These one or more passageways can be used to alter one or more physical properties of the support portion and/or a connecting leg (e.g., strength, bendability, etc.) and/or be used to contain one or more polymers and/or biological agents. FIG. 8 shows a stent leg or body portion having a cavity or internal passageway formed in it. Such passageways can be formed using the same various methods used to form the main body of the medical device, such as laser etching, etc. The internal passageways can be coated with polymer along with the surface of the medical device, as shown in FIG. 9A. In addition, the interior of the passageway can also or alternately be filled with a biological agent, as shown in FIG. 9B. These passageways can be filled in various ways. One non-limiting method is to place the medical device in a vacuum chamber and create a vacuum around the device. Biological agent or polymer is then introduced onto the medical device. The reduced pressure will draw the biological agent or polymer into the internal passageways. As can be appreciated, other methods can be used to incorporate polymer and/or biological agent in the cavity or internal passageway.

In another and/or additional non-limiting aspect of the present invention, many coating arrangements can be used on the medical device. When the one or more biological agents are inserted and/or impregnated in one or more internal structures, surface structures and/or micro-structures of the medical device, 1) one or more other coating materials can be applied at least partially over the one or more internal structures, surface structures and/or micro-structures of the medical device, and/or 2) one or more polymers can be combined with one or more biological agents. As such, the one or more biological agents can be 1) embedded in the structure of the medical device; 2) positioned in one or more internal structures of the medical device; 3) encapsulated between two polymer coatings; 4) encapsulated between the base structure and a polymer coating; 5) mixed in the base structure of the medical device that includes at least one polymer coating; or 6) one or more combinations of 1, 2, 3, 4 and/or 5.

In addition or alternatively, the one or more coating of the one or more polymers on the medical device can include 1) one or more coatings of non-porous polymers; 2) one or more coatings of a combination of one or more porous polymers and one or more non-porous polymers; 3) one or more coatings of one or more porous polymers and one or more coatings of one or more non-porous polymers; 4) one or more coating of porous polymer, or 5) one or more combinations of options 1, 2, 3 and 4. As can be appreciated different biological agents can be located in and/or between different polymer coating layers and/or on and/or the structure of the medical device, as described above. As can also be appreciated, many other and/or additional coating combinations and/or configurations can be used. The concentration of one or more biological agents, the type of polymer, the type and/or shape of internal structures in the medical device and/or the coating thickness of one or more biological agents can be used to control the release time, the release rate and/or the dosage amount of one or more biological agents; however, other or additional combinations can be used. As such, the biological agent and polymer system combination and location on the medical device can be numerous.

As can also be appreciated, one or more biological agents can be deposited on the top surface of the medical device to provide an initial uncontrolled burst effect of the one or more biological agents prior to 1) the control release of the one or more biological agents through one or more layers of polymer system that include one or more non-porous polymers and/or 2) the uncontrolled release of the one or more biological agents through one or more layers of polymer system. The one or more biological agents and/or polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer and/or layer of biological agent is generally at least about 0.01 µm and is generally less than about 150 µm. In one non-limiting embodiment, the thickness of a polymer layer and/or layer of biological agent is about 0.02-75 µm, more particularly about 0.05-50 µm, and even more particularly about 1-30 µm.

When the medical device includes and/or is coated with one or more biological agents such that at least one of the biological agents is at least partially controllably released from the medical device, the need or use of body-wide therapy for extended periods of time can be reduced or eliminated. In the past, the use of body-wide therapy was used by the patient long after the patient left the hospital or other type of medical facility. This body-wide therapy could last days, weeks, months or sometimes over a year after surgery.

In still another and/or additional non-limiting aspect of the present invention, the medical device of the present invention can be applied or inserted into a treatment area and 1) reduced use and/or extended use of body wide therapy after application or insertion of the medical device can be used or 2) no use and/or extended use of body wide therapy after application or insertion of the medical device is used. As can be appreciated, use and/or extended use of body wide therapy can be used after application or insertion of the medical device at the treatment area, in one non-limiting example, no body-wide therapy is needed after the insertion of the medical device into a patient.

In another and/or alternative non-limiting example, when short term use of body-wide therapy is needed or used after the insertion of the medical device into a patient, such short term use can be terminated after the release of the patient from the hospital or other type of medical facility, or one to two days or weeks after the release of the patient from the hospital or other type of medical facility; however, it will be appreciated that other time periods of body-wide therapy can be used. As a result of the use of the medical device of the present invention, the use of body-wide therapy after a medical procedure involving the insertion of a medical device into a treatment area can be significantly reduced or eliminated.

In another and/or additional non-limiting aspect of the present invention, controlled release of one or more biological agents from the medical device, when controlled release is desired, can be accomplished by using one or more non-porous polymer layers; however, other and/or additional mechanisms can be used to controllably release the one or more biological agents. The one or more biological agents are at least partially controllably released by molecular diffusion through the one or more non-porous polymer layers. When one or more non-porous polymer layers are used, the one or more polymer layers are typically biocompatible polymers; however, this is not required. The one or more non-porous polymers can be applied to the medical device without the use of chemical, solvents, and/or catalysts; however, this is not required. In one non-limiting example, the non-porous polymer can be at least partially applied by, but not limited to, vapor deposition and/or plasma deposition. The non-porous polymer can be selected so as to polymerize and cure merely upon condensation from the vapor phase; however, this is not required.

The non-porous polymer system can be mixed with one or more biological agents prior to being coated on the medical device and/or be coated on a medical device that previously included one or more biological agents; however, this is not required. The use or one or more non-porous polymer layers allow for accurate controlled release of the biological agent from the medical device. The controlled release of one or more biological agents through the non-porous polymer is at least partially controlled on a molecular level utilizing the motility of diffusion of the biological agent through the non-porous polymer. In one non-limiting example, the one or more non-porous polymer layers can include, but are not limited to, polyamide, parylene (e.g., parylene C, parylene N) and/or a parylene derivative.

In still another and/or additional non-limiting aspect of the present invention, controlled release of one or more biological agents from the medical device, when controlled release is desired, can be accomplished by using one or more polymers that form a chemical bond with one or more biological agents. In one non-limiting example, at least one biological agent includes trapidil, trapidil derivative or a salt thereof. The amount of biological agent that can be loaded with one or more polymers may be a function of the concentration of anionic groups and/or cationic groups in the one or more polymer.

For biological agents that are anionic, the concentration of biological agent that can be loaded on the one or more polymers is generally a function of the concentration of cationic groups (e.g., amine groups and the like) in the one or more polymer and the fraction of these cationic groups that can ionically bind to the anionic form of the one or more biological agents.

For biological agents that are cationic (e.g., trapidil, etc.), the concentration of biological agent that can be loaded on the one or more polymers is generally a function of the concentration of anionic groups in the one or more polymers, and the fraction of these anionic groups that can ionically bind to the cationic form of the one or more biological agents. As such, the concentration of one or more biological agent that can be bound to the one or more polymers can be varied by controlling the amount of hydrophobic and hydrophilic monomer in the one or more polymers, by controlling the efficiency of salt formation between the biological agent, and/or the anionic/cationic groups in the one or more polymers.

In still another and/or additional aspect of the present invention, a variety of polymers can be coated on the medical device and/or be used to form at least a portion of the medical device. The one or more polymers can be used on the medical for a variety of reasons such as, but not limited to, 1) forming a portion of the medical device, 2) improving a physical property of the medical device (e.g., improve strength, improve durability, improve biocompatibility, reduce friction, etc.), 3) forming a protective coating on one or more surface structures on the medical device, 4) at least partially forming one or more surface structures on the medical device, and/or 5) at least partially controlling a release rate of one or more biological agents from the medical device. As can be appreciated, the one or more polymers can have other or additional uses on the medical device. The one or more polymers can be porous, non-porous, biostable, biodegradable (i.e., dissolves, degrades, is absorbed, or any combination thereof in the body), and/or biocompatible.

Non-limiting examples of polymers that are considered to be biodegradable, bioresorbable, or bioerodable include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L(lactic acid) and/or poly-D Lactic acid) and/or copolymers thereof (e.g., DL-PLA), with and without additives (e.g., calcium phosphate glass), and/or other copolymers (e.g., poly(caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); polypropylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; polyethyl ester-co-carboxylate carbonate) (and/or other tyrosine derived polycarbonates); poly(iminocarbonate); poly(BPA-iminocarbonate); poly(trimethylene carbonate); poly(iminocarbonate-amide) copolymers and/or other pseudo-poly(amino acids); poly(ethylene glycol); poly(ethylene oxide); poly(ethylene oxide)/poly(butylene terephthalate) copolymer; polyCepsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); polypropylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above. Non-limiting examples of polymers that considered to be biostable include, but are not limited to, parylene; parylene c; parylene f; parylene n; parylene derivatives; maleic anyhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate/methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g., polystyrene); polyvinyl ethers) (e.g., polyvinyl methyl ether); polyvinyl ketones); poly(vinylidene halides) (e.g., polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g., polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g., polyvinyl acetate); and/or copolymers, blends, and/or composites of above. Non-limiting examples of polymers that can be made to be biodegradable and/or bioresorbable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers can be used. The thickness of each polymer layer is generally at least about 0.01 µm and is generally less than about 150 µm; however, other thicknesses can be used. In one non-limiting embodiment, the thickness of a polymer layer and/or layer of biological agent is about 0.02-75 µm, more particularly about 0.05-50 µm, and even more particularly about 1-30 µm. As can be appreciated, other thicknesses can be used. In one non-limiting embodiment, the medical device includes and/or is coated with parylene, PLGA, POE, PGA, PLLA, PAA, PEG, chitosan and/or derivatives of one or more of these polymers.

In another and/or alternative non-limiting embodiment, the medical device includes and/or is coated with a non-porous polymer that includes, but is not limited to, polyamide, parylene c, parylene n and/or a parylene derivative. In still another and/or alternative non-limiting embodiment, the medical device includes and/or is coated with poly(ethylene oxide), poly(ethylene glycol), and poly(propylene oxide), polymers of silicone, methane, tetrafluoroethylene (including TEFLON brand polymers), tetramethyldisiloxane, and the like.

In another and/or additional non-limiting aspect of the present invention, the medical device, when including and/or is coated with one or more biological agents, can include and/or can be coated with one or more biological agents that are the same or different in different regions of the medical device and/or have differing amounts and/or concentrations in differing regions of the medical device. For instance, the medical device can a) be coated with and/or include one or more biologicals on at least one portion of the medical device and at least another portion of the medical device is not coated with and/or includes biological agent; b) be coated with and/or include one or more biologicals on at least one portion of the medical device that is different from one or more biologicals on at least another portion of the medical device; c) be coated with and/or include one or more biologicals at a concentration on at least one portion of the medical device that is different from the concentration of one or more biologicals on at least another portion of the medical device; etc.

In still another and/or additional non-limiting aspect of the present invention, one or more surfaces of the medical device can be treated to achieve the desired coating properties of the one or more biological agents and one or more polymers coated on the medical device. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, freon, helium, hydrogen, etc. The plasma etching process can be used to clean the surface of the medical device, change the surface properties of the medical device so as to affect the adhesion properties, lubricity properties, etc. of the surface of the medical device. As can be appreciated, other or additional surface treatment processes can be used prior to the coating of one or more biological agents and/or polymers on the surface of the medical device.

In one non-limiting manufacturing process, one or more portions of the medical device are cleaned and/or plasma etched; however, this is not required. Plasma etching can be used to clean the surface of the medical device, and/or to form one or more non-smooth surfaces on the medical device to facilitate in the adhesion of one or more coatings of biological agents and/or one or more coatings of polymer on the medical device. The gas for the plasma etching can include carbon dioxide and/or other gasses. Once one or more surface regions of the medical device have been treated, one or more coatings of polymer and/or biological agent can be applied to one or more regions of the medical device. For instance, 1) one or more layers of porous or non-porous polymer can be coated on the medical device, 2) one or more layers of biological agent can be coated on the medical device, or 3) one or more layers of porous or non-porous polymer that includes one or more biological agents can be coated on the medical device. The one or more layers of biological agent can be applied to the medical device by a variety of techniques (e.g., dipping, rolling, brushing, spraying, particle atomization, etc.). One non-limiting coating technique is by an ultrasonic mist coating process wherein ultrasonic waves are used to break up the droplet of biological agent and form in a mist of very fine droplets. These fine droplets have an average droplet diameter of about 0.1-3 microns. The fine droplet mist facilitates in the formation of a uniform coating thickness and can increase the coverage area on the medical device.

In still yet another and/or additional non-limiting aspect of the present invention, one or more portions of the medical device can 1) include the same or different biological agents, 2) include the same or different amount of one or more biological agents, 3) include the same or different polymer coatings, 4) include the same or different coating thicknesses of one or more polymer coatings, 5) have one or more portions of the medical device controllably release and/or uncontrollably release one or more biological agents, and/or 6) have one or more portions of the medical device controllably release one or more biological agents and one or more portions of the medical device uncontrollably release one or more biological agents.

In still yet another and/or alternative non-limiting aspect of the present invention, the polymeric covering, the biological agent or any combination thereof can be biodegradable and has degradable properties. Suitable polymeric or other materials can have a certain tensile strength and/or other mechanical properties to enhance the physical properties of the stent; however, this is not required. Non-limiting examples of the properties of the polymeric coatings include, but are not limited to, 1) a polymer having sufficient mechanical properties that match the application, remaining sufficiently strong until the surrounding tissue has healed, 2) a polymer that does not invoke an inflammatory or toxic response, 3) a polymer that is metabolized in the body after fulfilling its purpose, leaving little no trace, 4) a polymer that is easily processable into the final product form, 5) a polymer that demonstrates acceptable shelf life, and/or 6) a polymer that is easily sterilized. As can be appreciated, when one or more biological agents are included on the medical device, the one or more biological agents can be used to at least partially control the rate of degradation of the biodegradable polymer when a biodegradable polymer is used; however, this is not required.

Suitable non-limiting examples of acceptable biodegradable polymers include: polyglycolide (PGA), polylactide (PLA), poly([epsilon]-caprolactone), poly(dioxanone) (a polyether-ester), poly(lactide-co-glycolide), as well as other homopolymers or copolymers of glycolide, lactide, caprolactone, p-dioxanone, and tri methylene carbonate.

In yet another and/or additional non-limiting aspect of the invention, the medical device can include a marker material that facilitates enabling the medical device to be properly positioned in a body passageway. The marker material is typically designed to be visible to electromagnetic waves (e.g., x-rays, microwaves, visible light, inferred waves, ultraviolet waves, etc.); sound waves (e.g., ultrasound waves, etc.); magnetic waves (e.g., MRI, etc.); and/or other types of electromagnetic waves (e.g., microwaves, visible light, inferred waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion; at ends of medical device; at or near transition of body portion and flaring section; etc.) of the medical device.

The location of the marker material can be on one or multiple locations on the medical device. The size of the one or more regions that include the marker material can be the same or different. The marker material can be spaced at defined distances from one another so as to form ruler like markings on the medical device to facilitate in the positioning of the medical device in a body passageway. The marker material can be a rigid or flexible material. The marker material can be a biostable or biodegradable material. When the marker material is a rigid material, the marker material is typically formed of a metal material (e.g., metal band, metal plating, etc.); however, other or additional materials can be used. The metal which at least partially forms the medical device can function as a marker material; however, this is not required.

The marker material can be coated with a polymer protective material; however, this is not required. When the marker material is coated with a polymer protective material, the polymer coating can be used to 1) at least partially insulate the marker material from body fluids, 2) facilitate in retaining the marker material on the medical device, 3) at least partially shielding the marker material from damage during a medical procedure and/or 4) provide a desired surface profile on the medical device. As can be appreciated, the polymer coating can have other or additional uses. The polymer protective coating can be a biostable polymer or a biodegradable polymer (e.g., degrades and/or is absorbed). The coating thickness of the protective coating polymer material, when used, is typically less than about 300 microns; however, other thickness can be used. In one non-limiting embodiment, the protective coating materials include parylene, PLGA, POE, PGA, PLLA, PAA, PEG, chitosan and/or derivatives of one or more of these polymers.

In another and/or additional non-limiting aspect of the present invention, other or additional manufacturing techniques can be used. The medical device can include one or more surface structures (e.g., pore, channel, pit, rib, slot, notch, bump, teeth, well, hole, groove, etc.). These structures can be at least partially formed by other types of technology.

In still another and/or additional non-limiting aspect of the invention, the medical device can be used in conjunction with one or more other biological agents that are not on the medical device. For instance, the success of the medical device can be improved by infusing, injecting or consuming orally one or more biological agents. Such biological agents can be the same and/or different from the one or more biological agents on and/or in the medical device. Such use of one or more biological agents are commonly used in systemic treatment of a patient after a medical procedure such as body wide after the medical device has been inserted in the treatment area can be reduced or eliminated by use of the novel alloy.

Although the medical device of the present invention can be designed to reduce or eliminate the need for long periods of body wide therapy after the medical device has been inserted in the treatment area, the use of one or more biological agents can be used in conjunction with the medical device to enhance the success of the medical device and/or reduce or prevent the occurrence of in-stent restenosis, vascular narrowing, and/or thrombosis. For instance, solid dosage forms of biological agents for oral administration, and/or for other types of administration (e.g., suppositories, etc.) can be used. Such solid forms can include, but are not limited to, capsules, tablets, effervescent tablets, chewable tablets, pills, powders, sachets, granules and gels. The solid form of the capsules, tablets, effervescent tablets, chewable tablets, pills, etc. can have a variety of shapes such as, but not limited to, spherical, cubical, cylindrical, pyramidal, and the like. In such solid dosage form, one or more biological agents can be admixed with at least one filler material such as, but not limited to, sucrose, lactose or starch; however, this is not required. Such dosage forms can include additional substances such as, but not limited to, inert diluents (e.g., lubricating agents, etc.).

When capsules, tablets, effervescent tablets or pills are used, the dosage form can also include buffering agents; however, this is not required. Soft gelatin capsules can be prepared to contain a mixture of the one or more biological agents in combination with vegetable oil or other types of oil; however, this is not required. Hard gelatin capsules can contain granules of the one or more biological agents in combination with a solid carrier such as, but not limited to, lactose, potato starch, corn starch, cellulose derivatives of gelatin, etc; however, this is not required. Tablets and pills can be prepared with enteric coatings for additional time release characteristics; however, this is not required. Liquid dosage forms of the one or more biological agents for oral administration can include pharmaceutically acceptable emulsions, solutions, suspensions, syrups, elixirs, etc.; however, this is not required. In one non-limiting embodiment, when at least a portion of one or more biological agents is inserted into a treatment area (e.g., gel form, paste form, etc.) and/or provided orally (e.g., pill, capsule, etc.) and/or anally (suppository, etc.), one or more of the biological agents can be controllably released; however, this is not required. In one non-limiting example, one or more biological agents can be given to a patient in solid dosage form and one or more of such biological agents can be controllably released from such solid dosage forms. In another and/or alternative non-limiting example trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof are given to a patient prior to, during and/or after the insertion of the medical device in a treatment area.

Certain types of biological agents may be desirable to be present in a treated area for an extended period of time in order to utilize the full or nearly full clinical potential the biological agent. For instance, trapidil and/or trapidil derivatives is a compound that has many clinical attributes including, but not limited to, anti-platelet effects, inhibition of smooth muscle cells and monocytes, fibroblast proliferation and increased MAPK-1 which in turn deactivates kinase, a vasodilator, etc. These attributes can be effective in improving the success of a medical device that has been inserted at a treatment area. In some situations, these positive effects of trapidil and/or trapidil derivatives need to be prolonged in a treatment area in order to achieve complete clinical competency. Trapidil and/or trapidil derivatives has a half life in vivo of about 2-4 hours with hepatic clearance of 48 hours. In order to utilize the full clinical potential of trapidil and/or trapidil derivatives, trapidil and/or trapidil derivatives should be metabolized over an extended period of time without interruption; however, this is not required.

By inserting trapidil and/or trapidil derivatives in a solid dosage form, the trapidil and/or trapidil derivatives could be released in a patient over extended periods of time in a controlled manner to achieve complete or nearly complete clinical competency of the trapidil and/or trapidil derivatives. These biological agents can be at least partially encapsulated in one or more polymers, as with the biological agents on the medical device described above. The rate of degradation of the polymer is principally a function of 1) the water permeability and solubility of the polymer, 2) chemical composition of the polymer and/or biological agent, 3) mechanism of hydrolysis of the polymer, 4) the biological agent encapsulated in the polymer, 5) the size, shape and surface volume of the polymer, 6) porosity of the polymer, 7) the molecular weight of the polymer, 8) the degree of cross-linking in the polymer, 9) the degree of chemical bonding between the polymer and biological agent, and/or 10) the structure of the polymer and/or biological agent. As can be appreciated, other factors may also affect the rate of degradation of the polymer.

When the one or more polymers are biostable, the rate at when the one or more biological agents are released from the biostable polymer is a function of 1) the porosity of the polymer, 2) the molecular diffusion rate of the biological agent through the polymer, 3) the degree of cross-linking in the polymer, 4) the degree of chemical bonding between the polymer and biological agent, 5) chemical composition of the polymer and/or biological agent, 6) the biological agent encapsulated in the polymer, 7) the size, shape and surface volume of the polymer, and/or 8) the structure of the polymer and/or biological agent. As can be appreciated, other factors may also affect the rate of release of the one or more biological agents from the biostable polymer. Similar or different polymers than those described above for use with the medical device can be used. As can be appreciated, the at least partially encapsulated biological agent can be introduced into a patient by means other than by oral introduction, such as, but not limited to, injection, topical applications, intravenously, eye drops, nasal spray, surgical insertion, suppositories, intrarticularly, intraocularly, intranasally, intradermally, sublingually, intravesical˄, intrathecally, intraperitoneally, intracranially, intramuscularly, subcutaneously, directly at a particular site, and the like.

One or more biological agents, when used, can be released from the medical device for at least about one week after the medical device is inserted in the body of a patient, more typically at least about two weeks after the medical device is inserted in the body of a patient, and even more typically about one week to one year after the medical device is inserted in the body of a patient. As can be appreciated, the time frame that one or more of the biological agents can be released from the medical device can be longer or shorter. The time period for the release of two or more biological agents from the medical device can be the same or different.

The type of the one or more biological agents used on the medical device, the release rate of the one or more biological agents from the medical device, and/or the concentration of the one or more biological agents being released from the medical device during a certain time period is typically selected to deliver one or more biological agents directly to the area of disease after the medical device has been implanted; however, this is not required. In one non-limiting design of medical device, the medical device releases one or more biological agents over a period of time after being inserted in the body after the medical device has been implanted. In another non-limiting design of medical device, the medical device releases one or more biological agents over a period of time after being inserted in the body so that no further drug therapy is required about two weeks to one month after the medical device has been implanted.

In one non-limiting design of medical device, the medical device releases one or more biological agents over a period of up to one day after the medical device has been implanted. In still yet another non-limiting design of medical device, the medical device releases one or more biological agents over a period of up to one week after the medical device has been implanted. In further another non-limiting design of medical device, the medical device releases one or more biological agents over a period of up to two weeks after the medical device has been implanted. In still a further non-limiting design of medical device, the medical device releases one or more biological agents over a period of up to one month after the medical device has been implanted. In yet a further non-limiting design of medical device, the medical device releases one or more biological agents over a period of up to one year after the medical device has been implanted. As can be appreciated, the time or release of one or more biological agents from the medical device can be more than one year after the medical device has been implanted.

Typically the introduction of one or more biological agents used for anti-platelet and/or anti-coagulation therapy from a source other than the medical device is about one day after the medical device has been implanted in a patent, and typically up to about one week after the medical device has been implanted in a patent, and more typically up to about one month after the medical device has been implanted in a patent; however, it can be appreciated that periods of up to 2-3 months or more can be used.

The stent is at least partially formed of an alloy that includes a majority of Ta and W. For example, the metal alloy can include about 90-97.5 weight percent Ta and 2.5-10 weight percent W (i.e., 92.5% Ta-7.5% W). The stent can be formed by use of several processes. For instance, a tube of TaW alloy can be formed by a vacuum arc melting process in which the formed alloy extruded and processed into a rod, or metal power can be consolidated into the alloy isostatic pressing and sintering at high temperatures under a vacuum. The formed rod cut into lengths of about 20-48 inches (i.e., 36 inches). The diameter of the rod may be up to about 0.1 inches (e.g., 0.0625 inches). The solid rod can be drilled to form a tube having the desired inner and outer diameters and wall thickness. The tube can be chemically cleaned (e.g., 2-98% nitric acid and 2-98% hydrochloric acid, 50% nitric acid and 50% hydrochloric acid). Generally, the cut tube is wrapped in niobium foil to reduce contamination if shipped to another location for annealing. The TaW alloy is annealed at about 2600-2800° F. under a vacuum of no greater that about 5-10 Torr. Horizontal or vertical furnaces can be used for the annealing process, for a period of about 60 minutes. The annealed tube is processed to a final diameter (e.g., pilgering and drawing of no more than about 60% working reduction between annealing processes, etc.). The drawing of the tube can be at room or ambient temperature (i.e., 60-90° F.). The tube may be processed until the wall thickness of the tube up to about 0.0025 inches (i.e., 0.0018-0.002 inches). For example, the original tube diameter may be about 0.003-0.008 inches, and is preferably processed to a thickness of no more than about 0.0025 inches, although the original diameter of the tube can of course be greater than this.

Once the tube has been processed to its final or near final diameter, the tube is cleaned and polished by an electro-polishing process using sulfuric acid and hydrofluoric acid (i.e., 60-95% sulfuric and 5-40 hydrofluoric, 85% sulfuric and 15% hydrofluoric at 60-100° F. and at a current of 15-30 milliamps). After the tube is polished, the medical device can be formed by cutting the tube (e.g., laser cutting at about 2800-32000° C. in a helium and/or argon containing environment) As can be appreciated, other or additional manufacturing processes can be used to form the stent. The grain size of the metal alloy is about 8-14 ASTM. The stent can include one or more coating and/or one or more surface structures and/or micro-structures. Other processing steps for the TaW alloy that can be used in the present invention are disclosed in U.S. Pat. Publ. No. 2006/0264914, which is incorporated herein.

One non-limiting object of the present invention is the provision of a medical device that is formed of a metal alloy that includes zirconium, tantalum, niobium and/or tungsten.

Still another and/or additional non-limiting object of the present invention is the provision of a medical device having improved procedural success rates.

Yet another and/or additional non-limiting object of the present invention is the provision of a medical device that is simple and cost effective to manufacture.

Another and/or additional non-limiting object of the present invention is the provision of a medical device that is at least partially formed of, contains, and/or is coated one or more biological agents.

Still yet another and/or additional non-limiting object of the present invention is the provision of a medical device that controllably releases one or more biological agents.

A further and/or additional non-limiting object of the present invention is the provision of a medical device that is at least partially coated with one or more polymer coatings.

Yet a further and/or additional non-limiting object of the present invention is the provision of a medical device that has one or more polymer coatings to at least partially control the release rate of one or more biological agents.

Still a further and/or additional non-limiting object of the present invention is the provision of a medical device that at least partially control the release rate of one or more biological agents by molecular diffusion.

A further and/or additional non-limiting object of the present invention is the provision of a medical device that has one or more polymer coatings and/or one or more coating or biological agent that is used to at least partially control the rate of degradation of a biodegradable material on the medical device.

Another and/or additional non-limiting object of the present invention is the provision of a medical device that is in the form of a stent.

Yet another and/or additional non-limiting object of the present invention is the provision of a medical device that includes one or more markers.

Still yet another and/or additional non-limiting object of the present invention is the provision of a medical device that includes and/or is used with one or more physical hindrances.

Still a further and/or additional non-limiting object of the present invention is the provision of a medical device that can be used in conjunction with one or more biological agents not on or in the medical device.

Still yet another and/or additional non-limiting object of the present invention is the provision of a medical device that includes one or more structural component having varying thicknesses, configurations, and/or surface features so as to affect rate and/or degree at which the medical expands and/or retains its shape in a body passageway.

These and other advantages will become apparent to those skilled in the art upon the reading and following of this description taken together with the accompanying drawings.

What is claimed is:

1. A process for producing a stent that has design features that include differentiated wall thicknesses across the length of the stent and geometrically-based shapes to enhance the mechanical properties of said stent, said process comprising the steps of:
   a) providing a non-clad metal tube, about 100 weight percent of said metal tube formed of an alloy of 90-97.5% tantalum and 2.5-10% tungsten, said metal having a grain size of at least about 8 ASTM;
   b) chemically cleaning said metal tube by a solution that includes nitric acid and hydrochloric acid;
   c) annealing said chemically cleaned tube at a temperature of about 2600° F.-2800° F., said step of annealing occurring under a vacuum of no greater that about 10 Torr;
   d) cleaning and polishing said annealed tube by an electro-polishing process, said electro-polishing process including a solution that includes sulfuric acid and hydrofluoric acid having a temperature of about 60-100° F., said electro-polishing process conducted in the presence of a current of 15-30 milliamps, said step of electro-polishing performed in such a manner as to prevent said metal tube from becoming brittle and to prevent excess hydrogen, oxygen and nitrogen from entering said metal tube;
   e) cutting said tube to a desired length after said cleaning and polishing step; and,
   f) cutting said tube to form said stent after said tube is cut to said desired length, said step of cutting said tube into said stent includes a laser cutting process in an environment that includes one or more gasses selected from the group consisting of helium and argon, said stent having a plurality of metal support portions and a plurality of metal connecting legs, said metal connecting legs connecting together a plurality of metal support portions, said metal support portions and metal connecting legs forming a mesh in a peripheral wall of said cut tube, a plurality of said metal support portions having an S-shape, a Z-shape, an XZ-shape, a VU shape, an XS shape, or a YU-shape configuration, a plurality of said metal support portions having a thickness of 0.0012-0.007 inch, a plurality of said metal support portions and connecting legs having multiple thicknesses along a longitudinal length of said metal support portions and connecting legs, a thinnest portion of said metal support portions having a thickness as small as about 0.0012 inch and a thickest portion of said metal support portions being about 0.004-0.007 inch, said wall thickness of said metal tube has a thickness so that its physiological presence in a body passage is negligible thereby preventing turbulent flow of fluid as the fluid passes by said stent positioned in the body passageway.

2. The process as defined in claim 1, wherein said metal includes 90-93% tantalum and 7-10% tungsten.

3. The process as defined in claim 2, wherein said metal includes 92.5 wt. % tantalum and 7.5 wt. % tungsten.

4. The process as defined in claim 1, including the further step of forming a plurality of surface modifications in one or more structures selected from the group consisting of metal support portions and metal connecting legs, said surface modifications including a channel, said channel having a single opening at only one end of said channel, said single opening located at a surface of said stent.

5. The process as defined in claim 3, including the further step of forming a plurality of surface modifications in one or more structures selected from the group consisting of metal support portions and metal connecting legs, said surface modifications including a channel, said channel having a single opening at only one end of said channel, said single opening located at a surface of said stent.

6. The process as defined in claim 4, including the further step of adding at least one of a polymer and a biological agent to one or more structures selected from the group consisting of metal support portions and metal connecting legs, a plurality of said channels including said biological agent, at least one of said channels including at least one of a polymer and a biological agent.

7. The process as defined in claim 5, including the further step of adding at least one of a polymer and a biological agent to one or more structures selected from the group consisting of metal support portions and metal connecting legs, a plurality of said channels including said biological agent, at least one of said channels including at least one of a polymer and a biological agent.

8. The process as defined in claim 6, wherein said polymer overlies a plurality of said channels that includes said biological agent so as to control a release rate of said biological agent from said plurality of channels.

9. The process as defined in claim 7, wherein said polymer overlies a plurality of said channels that includes said biological agent so as to control a release rate of said biological agent from said plurality of channels.

10. A process for producing a stent that has design features that include differentiated wall thicknesses across the length of the stent and geometrically-based shapes to enhance the mechanical properties of said stent, said process comprising the steps of:
   a) providing a non-clad metal tube, about 100 weight percent of said metal tube formed of an alloy of 90-93% tantalum and 7-10% tungsten, said metal having a grain size of at least about 8 ASTM;
   b) chemically cleaning said metal tube by a solution that includes nitric acid and hydrochloric acid;
   c) annealing said chemically cleaned tube at a temperature of about 2600° F.-2800° F., said step of annealing occurring under a vacuum of no greater that about 10 Torr;
   d) cleaning and polishing said annealed tube by an electro-polishing process, said electro-polishing process including a solution that includes sulfuric acid and hydrofluoric acid having a temperature of about 60-100° F., said electro-polishing process conducted in the presence of a current of 15-30 milliamps, said step of electro-polishing performed in such a manner as to prevent said metal tube from becoming brittle and to prevent excess hydrogen, oxygen and nitrogen from entering said metal tube;

e) cutting said tube to a desired length after said cleaning and polishing step; and, f) cutting said tube to form said stent after said tube is cut to said desired length, said step of cutting said tube into said stent includes a laser cutting process in an environment that includes one or more gasses selected from the group consisting of helium and argon, said stent having a plurality of metal support portions and a plurality of metal connecting legs, said metal connecting legs connecting together a plurality of metal support portions, said metal support portions and metal connecting legs forming a mesh in a peripheral wall of said cut tube, a plurality of said metal support portions having a thickness of 0.0012-0.007 inch, a plurality of said metal support portions and connecting legs having multiple thicknesses along a longitudinal length of said metal support portions and connecting legs, a thinnest portion of said metal support portions having a thickness as small as about 0.0012 inch and a thickest portion of said metal support portions being about 0.004-0.007 inch, said wall thickness of said metal tube has a thickness so that its physiological presence in a body passage is negligible thereby preventing turbulent flow of fluid as the fluid passes by said stent positioned in the body passageway.

* * * * *